United States Patent
Furman et al.

(10) Patent No.: US 7,659,973 B2
(45) Date of Patent: Feb. 9, 2010

(54) WAFER INSPECTION USING SHORT-PULSED CONTINUOUS BROADBAND ILLUMINATION

(75) Inventors: Dov Furman, Rehovot (IL); Shai Silberstein, Rishon Le-Zion (IL)

(73) Assignee: Applied Materials Southeast Asia, Pte Ltd., Singapore (SG)

( * ) Notice: Subject to any disclaimer, the term of this patent is extended or adjusted under 35 U.S.C. 154(b) by 0 days.

(21) Appl. No.: 11/684,191

(22) Filed: Mar. 9, 2007

(65) Prior Publication Data
US 2007/0273945 A1 Nov. 29, 2007

Related U.S. Application Data

(60) Provisional application No. 60/808,816, filed on May 26, 2006.

(51) Int. Cl.
*G01N 21/88* (2006.01)
(52) U.S. Cl. .................. 356/237.2; 250/472
(58) Field of Classification Search ... 356/237.2–237.6; 250/559.41–559.48
See application file for complete search history.

(56) References Cited

U.S. PATENT DOCUMENTS

| | | | | |
|---|---|---|---|---|
| 3,790,280 A | * | 2/1974 | Heinz et al. | 356/71 |
| 4,588,293 A | * | 5/1986 | Axelrod | 356/237.2 |
| 4,619,508 A | | 10/1986 | Shibuya et al. | |
| 5,264,912 A | | 11/1993 | Vaught et al. | |
| 5,302,999 A | | 4/1994 | Oshida et al. | |
| 5,471,066 A | * | 11/1995 | Hagiwara | 250/559.48 |
| 5,583,632 A | * | 12/1996 | Haga | 356/129 |
| 5,970,168 A | | 10/1999 | Montesanto et al. | |
| 6,369,888 B1 | | 4/2002 | Karpol et al. | |
| 6,710,868 B2 | | 3/2004 | Guetta | |
| 6,774,991 B1 | * | 8/2004 | Danko | 356/237.4 |
| 6,796,699 B2 | | 9/2004 | Birk et al. | |
| 6,892,013 B2 | | 5/2005 | Furman et al. | |
| 6,919,958 B2 | * | 7/2005 | Stanke et al. | 356/237.2 |
| 2002/0054291 A1 | | 5/2002 | Tsai et al. | |

(Continued)

OTHER PUBLICATIONS

"Aberration", Columbia Encyclopedia, 2008, New York, NY, Columbia University Press.*

(Continued)

*Primary Examiner*—Gregory J Toatley, Jr.
*Assistant Examiner*—Rebecca C Slomski
(74) *Attorney, Agent, or Firm*—Sonnenschein Nath & Rosenthal LLP Dority & Manning, PA

(57) ABSTRACT

An inspection system may be configured to inspect objects, such as semiconductor wafers, using narrow-pulse broadband illumination. The illumination may be obtained in some embodiments using a laser configured to emit light into a material having a spectral broadening effect. The inspection system can include various filters which may be selectively placed in the illumination and/or imaging path in order to tune the spectrum of light impinging on the wafer and the light that is detected. The filters may include selectable filters, fixed filters, and filters whose characteristics can be adjusted in-place. In some embodiments, filters may be used to match the illumination/detection spectra of different tools. Additionally, the broadband illumination may be tuned between inspections and/or during inspections for best results. The system may support Fourier filtering whereby light, related to repetitive features of the object and in one or more wavelength sub-bands of the illumination, may be filtered.

27 Claims, 11 Drawing Sheets

U.S. PATENT DOCUMENTS

| | | |
|---|---|---|
| 2003/0227618 A1 | 12/2003 | Some |
| 2004/0146295 A1 | 7/2004 | Furman et al. |
| 2004/0252297 A1 | 12/2004 | Fairley et al. |
| 2005/0110987 A1 | 5/2005 | Furman et al. |
| 2006/0012781 A1 | 1/2006 | Fradkin et al. |
| 2007/0008519 A1* | 1/2007 | Naftali et al. ............ 356/237.2 |

OTHER PUBLICATIONS

European Search Report—2 pages Nov. 2, 2007 for application EP 07 25 2110.

European Search Report—9 pages Nov. 2, 2007 for application EP 07 25 2110.

Fuchs et al., U.S. Appl. No. 11/410,276, filed Apr. 24, 2006, Printed Fourier Filtering In Optical Inspection Tools.

Furman et al., U.S. Appl. No. 11/503,859, filed Aug. 14, 2006, Speckle Reduction Using A Fused Fiber Bundle and Light Guide.

"Spectral Extent and Pulse Shape of the Laser Pulse Supercontinuum for Ultrashort", Manassah et al., IEEE Journal of Quantum Electronics, vol. QE-22, No. 1, Jan. 1986, pp. 197-204.

"Supercontinuum Generation in Photonic Crystal Fibers", Hansen et al. Crystal Fibre A/S, www.crystal-fibre.com, pp. 1-11, 2005.

Dingel et al., "Speckle Reduction with Virtual Incoherent Laser Illumination Using a Modified Fiber Array", Optik, Wissenschaftliche Verlag GmbH, Stuttgart, Germany, vol. 94, No. 3, Sep. 1993, pp. 132-136.

Partial European Search Report—5 pages for EP 07 25 2110 dated Jun. 9, 2007.

* cited by examiner (FROM FIGURE 1A)

(6) ACQUIRE A DIGITAL INSPECTION IMAGE OF THE FIELD OF VIEW OF THE INSPECTED WAFER DIE(S) USING THE THE PHOTO DETECTOR(S) AND SAVE THE DIGITAL INSPECTION IMAGE DATA IN MEMORY (7) REPEAT STEPS (3) THROUGH (6) FOR THE NEXT FIELDS OF VIEW TO FORM A STRIP FOR THE INSPECTED WAFER DIE OR INSPECTED WAFER DIES (8) OBTAIN OR GENERATE A REFERENCE IMAGE OR IMAGES FROM MEMORY, THE IMAGE(S) CORRESPONDING TO THE STRIP OF THE INSPECTED DIE(S)

(9) PROCESS THE INSPECTION IMAGE AND CORRESPONDING REFERENCE IMAGE(S) TO DETERMINE THE EXISTENCE OF ONE OR MORE DEFECTS

(10) CONFIRM THE EXISTENCE OR NON-EXISTENCE OF A DEFECT IN THE STRIP AND SAVE THE DEFECT DATA IN MEMORY

(11) REPEAT STEPS (7) THROUGH (10) FOR ALL FIELDS OF VIEW WITHIN EACH INSPECTED STRIPS AND FOR ALL STRIPS WITHIN THE WAFER

FIGURE 1B

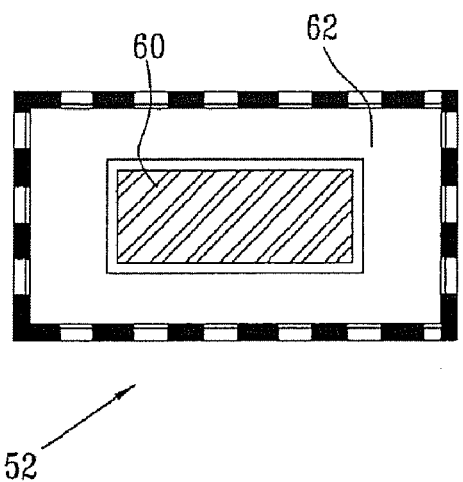
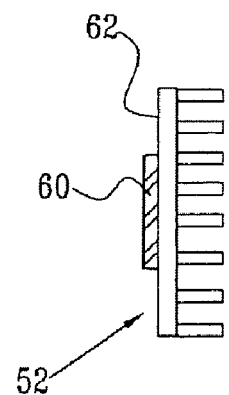
FIGURE 3A
FIGURE 3B
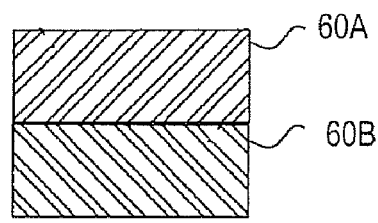
FIGURE 4

WAFER INSPECTION USING SHORT-PULSED CONTINUOUS BROADBAND ILLUMINATION

CROSS-REFERENCE TO OTHER APPLICATIONS

This application claims priority to U.S. Provisional Patent Application No. 60/808,816, filed May 26, 2006, and hereby incorporates by reference that provisional patent application in its entirety.

BACKGROUND

In the field of optical inspection of objects such as semiconductor wafers, reticles, flat-panel displays, and other devices, the particular illumination source that is used can greatly affect the inspection results.

For example, illumination may be characterized as narrowband illumination or broadband illumination in the wavelength domain. Illumination may be further characterized as long-pulsed (i.e. long pulse in the time domain) or short-pulsed (i.e. short pulse in the time domain). Together, the characteristics are shown in FIG. 12, which also shows where some exemplary sources generally fall in the characterizations.

Some inspection systems use lamps, some systems use continuous lasers, and some systems use short-pulsed lasers. Inspection systems that utilize lamps may select narrowband or broadband illumination. However, lamps generally must be continuously illuminated or long-pulsed in the time domain. Although lamps may provide options with regard to the type of illumination, when high power illumination is required, short-pulsed lasers may be preferred. For instance, short pulsed lasers may be especially relevant for 2-D imaging. Furthermore, short-pulsed lasers may be advantageous in that the short illumination time reduces errors caused by pixel smear. However, presently-existing inspection systems that utilize short-pulsed lasers may suffer from certain disadvantages.

While lamps, as noted above, may be used for broadband inspection, presently-existing systems that utilize pulsed lasers provide for a relatively narrow bandwidth of illumination. This may lead to problems in the inspection. One such problem is "color variation." For instance, differences in the thickness of layers in a semiconductor wafer may lead to differences in the colors and/or intensity of layers. In monochromatic imaging, the differences may appear as different intensities, while in polychromatic imaging, the differences may appear as different colors. In any event, any such intensity/color differences can trigger false alarms even if the changes in thickness in the wafer are within tolerated ranges. Another problem with narrowband laser illumination is speckle caused by interference between coherent illuminating photons. Various schemes have been proposed for reducing speckle through additional optical components. However, the use of such components may deteriorate the illumination quality and/or its intensity and result in a degraded image.

Accordingly, a need remains for an inspection system that can provide improved inspection results.

SUMMARY AND ADVANTAGES

Objects and advantages of the present invention will be apparent to one of skill in the art upon careful review of this disclosure, and include providing improved methods and systems of inspecting objects such as semiconductor wafers using short-pulsed broadband illumination.

Exemplary embodiments of the presently-disclosed technology inspect objects using broadband illumination provided by a short-pulsed laser. For example, a short-pulsed laser may be combined with any suitable non-linear material or device to broaden the laser's illumination spectrum. For example, light from the laser may be directed into a material having a so-called "supercontinuum effect," such as a single photonic crystal fiber or a bundle of photonic crystal fibers. Additional components in the inspection system may be selected and configured to provide optimal inspection conditions. For example, one or more filters may be used to tune the illumination from the laser and/or to filter light prior to detection.

A wafer inspection system can comprise an imager operative to image at least one object, such as a wafer, while the wafer is illuminated. The inspection system can further include an illumination source that is configured to illuminate the wafer with a pulse of illumination no longer than about 1 microsecond in temporal length and having a continuous spectral range of at least 20 nm. For example, the wafer may be in motion along a travel path whereby the wafer and the imager are moving relative to one another. For instance, the wafer may be moving on a stage that is included as part of a transporter. Alternatively or additionally, the system may be configured such that the imager or at least some components thereof are movable so that different portions of the wafer can be imaged. However, any discussion herein of the particular type of movement of the wafer and/or other system components is not meant to be limiting.

For example, the illumination source may comprise a pulsed laser that is broadened to a spectral range falling within about 180 to about 450 nm. The illumination source may comprise a laser and a non-linear optical component having a spectral broadening effect. For instance, the non-linear optical component may comprise one or more photonic crystal fibers. In some embodiments, the component comprises a bundle of photonic crystal fibers, and some of the fibers have different optical lengths from one another. In other embodiments, regular/normal fused silica fibers can be used, with the non-linearity coefficients of fused silica used for the broadening effect.

The inspection system may include one or more filters configured to pass one or more specified ranges of wavelengths, with the filter(s) placed in one or more of the optical paths in the inspection system. By placing, removing, and/or adjusting the filter(s), wavelength bands may be selected based on factors such as the optical characteristics of the wafer.

For instance, the filter(s) may be placed in the imaging path between the wafer and at least one of the detectors in the imager. As another example, in some embodiments, filter(s) may be placed in the illumination path between the source and the wafer. Regardless of placement, some or all of the filter(s) may be variable filters whereby the optical characteristics of the filter(s) can be tuned by the inspection system, for instance, to select different wavelength bands to be passed/blocked by the filter(s) during the inspection process. Additionally or alternatively, wavelength bands may be selected by placing one or more filters with fixed characteristics in the optical path and/or removing them from the optical path.

In some embodiments, the inspection system may include one or more optical elements positioned to form an image of the wafer and having a Fourier plane. One or more filter masks may be placed at a Fourier plane, with the mask(s)

configured to block light corresponding to repetitive features of the wafer, where the light falls in a continuous wavelength band.

In some embodiments, one or more of the masks include a plurality of blocking areas, with some of the blocking areas blocking light in different wavelength sub-bands within the continuous wavelength band than other blocking areas. In other embodiments, each of a plurality of masks may include blocking areas for repetitive features in different wavelength sub-bands.

In some embodiments, the system may include one or more optical elements configured to focus at least one wavelength sub-band at a different point from another wavelength sub-band. For example, the system may include elements whereby light of a first wavelength sub-band is focused on the surface of the wafer while light of a second wavelength sub-band is focused beneath the surface of the wafer.

A method of inspecting a wafer using an optical inspection system can include emitting a pulse of light, such as from a laser, with the pulse no longer than about one microsecond in time. The emitted pulse can be directed into a nonlinear optical element to obtain broadband illumination having a continuous spectral range of at least 20 nm. The broadband illumination may then be directed towards a wafer (or other object) under inspection. Then, at least one image of at least a portion of the wafer can be captured using an imager that includes at least one detector. The nonlinear optical component may comprise a bundle of photonic crystal fibers, which may have different optical lengths from one another or a single fiber. Alternatively, the fibers may be normal fused silica fibers. Directing the broadband illumination can include focusing the illuminating beam so that at least one wavelength band is focused at a different location than anther wavelength band in the beam.

The method can include tuning the spectrum of the inspection system to a desired spectrum which may, for example, be selected based on the optical characteristics of the wafer and/or the particular inspection being undertaken. For example, the method may comprise determining a plurality of spectra for use in inspecting at least two different regions of a wafer. The system may then be tuned to a first spectrum for a first region, a second spectrum for a second region, and so on. The spectra may be chosen based at least in part on data including the degree of color variation in the regions of the wafer.

The spectrum may be tuned in any suitable way. For instance, the spectrum may be tuned by filtering light at any suitable point or points. For example, a filter may be placed in the optical path between the nonlinear optical element and the wafer, between the wafer and the detector(s), or in both places. Filters may be placed and removed to adjust the spectrum. In other embodiments, the spectrum may be adjusted by tuning the characteristics of a variable filter that is in the optical path.

In some embodiments, the inspection process may include eliminating the effects of repetitive features in the wafer in order that defects might more clearly stand out. A method of eliminating repetitive features can include illuminating a wafer having one or more repetitive features with broadband illumination. One or more images of the wafer can be formed using at least one optical element having a Fourier plane. One or more filter masks can be placed at the Fourier plane, with the mask(s) configured to block light containing information related to the repetitive features at a plurality of wavelength sub-bands within the broadband illumination.

For example, at least one of the masks can include blocking areas that block light different wavelength sub-bands than other blocking areas. For instance, a single mask may include multiple layers, with each layer containing blocking elements corresponding to a different sub-band. In other embodiments, multiple filter masks may be used for multiple sub-bands. The image of the wafer may be split into a plurality of images corresponding to different sub-bands, with the light comprising each split image having its own optical path. Filter masks for each sub-band split image may be placed in the corresponding optical path.

BRIEF DESCRIPTION OF THE DRAWINGS

A full and enabling disclosure including the best mode of practicing the appended claims and directed to one of ordinary skill in the art is set forth more particularly in the remainder of the specification. The specification makes reference to the appended figures, in which:

FIGS. 1A-1B are a flowchart showing exemplary steps in an optical inspection process;

FIGS. 3A-B illustrate an exemplary photodetector;

FIG. 4 illustrates an exemplary arrangement of detection components in an optical inspection system;

Use of like reference numerals in different features is intended to illustrate like or analogous components.

DETAILED DESCRIPTION OF THE PREFERRED EMBODIMENTS

Reference will now be made in detail to various and alternative exemplary embodiments and to the accompanying drawings, with like numerals representing substantially identical structural elements. Each example is provided by way of explanation, and not as a limitation. In fact, it will be apparent to those skilled in the art that modifications and variations can be made without departing from the scope or spirit of the disclosure and claims. For instance, features illustrated or described as part of one embodiment may be used on another embodiment to yield a still further embodiment. Thus, it is intended that the present disclosure includes modifications and variations as come within the scope of the appended claims and their equivalents.

Embodiments of the methods and systems for fast on-line electro-optical detection of wafer defects discussed herein generally relate to the use of short-pulsed, broadband illumination in optical inspection tools. Exemplary embodiments of inspection tools are discussed in U.S. patent application Ser.

No. 10/345,097, filed Jan. 15, 2003. Application Ser. No. 10/345,097 is incorporated by reference for all purposes herein. However, the principles and teachings discussed herein are applicable to other inspection tools, as well, and the discussion of particular components and steps is intended to be for purposes of example only.

Figure 1A:
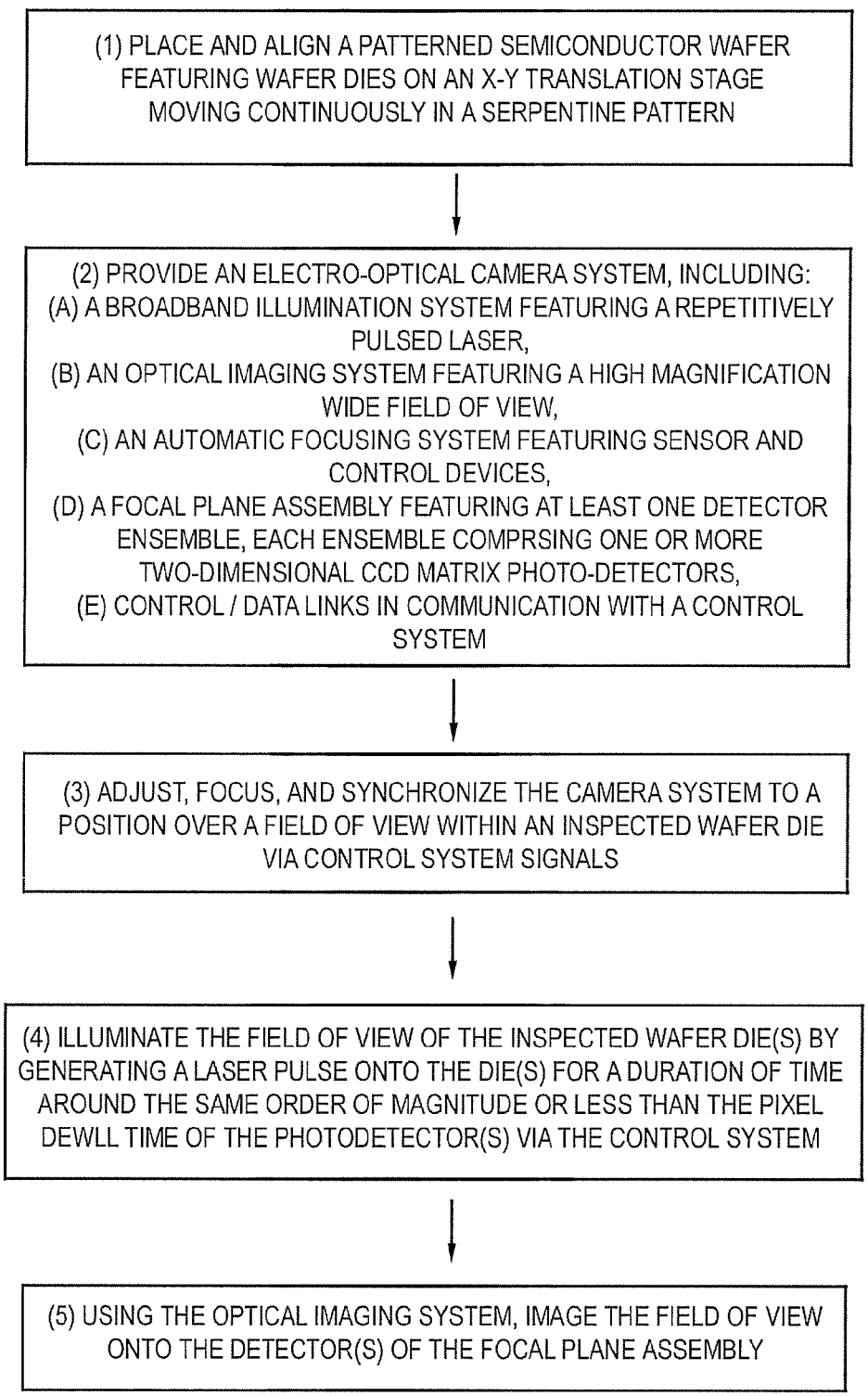

Referring now to the drawings, FIG. 1 is a flow diagram of an exemplary embodiment of a method for fast electro-optical on-line detection of wafer defects. In FIG. 1, each generally applicable, principal step of an exemplary method of the present subject matter is numbered and enclosed inside a frame. Sub-steps representing further of an indicated principal step of the method are indicated by a letter in parentheses. FIGS. 2 through 11 are schematic diagrams illustrating exemplary embodiments of the system, and exemplary components for implementing embodiments of the method.

In Step 1 of the method, a patterned semiconductor wafer 12 featuring a plurality of wafer dies 14, is placed and aligned on a continuous moving XY translation stage 16. This is shown in system 10 of FIG. 2, which is a schematic diagram illustrating an exemplary embodiment of an inspection system. XY translation stage 16 moves wafer 12 typically in a serpentine pattern beneath an optical imaging system 18. However, other movement patterns could be used. Movement of XY translation stage 16 (and therefore movement of wafer 12) is synchronized with action of a multi-component camera system by a central control system 20 via control/data links 22, in such a way that wafer 12 moves the equivalent of one field of view 24 during a CCD matrix photo-detector frame time. For example, the frame time and motion may be synchronized so that the wafer moves only on the order of about $10^{-2}$ of a single pixel during exposure to an illumination system 26, thereby resulting in little to no image smear or loss of image resolution.

In Step 2, a multi-component electro-optical camera system is provided, including (a) an illumination system 26, (b) an optical imaging system 18, (c) an automatic focusing system 28, (d) a focal plane assembly 30, and (e) respective system control/data links, in communication with central control system 20.

Figure 2:
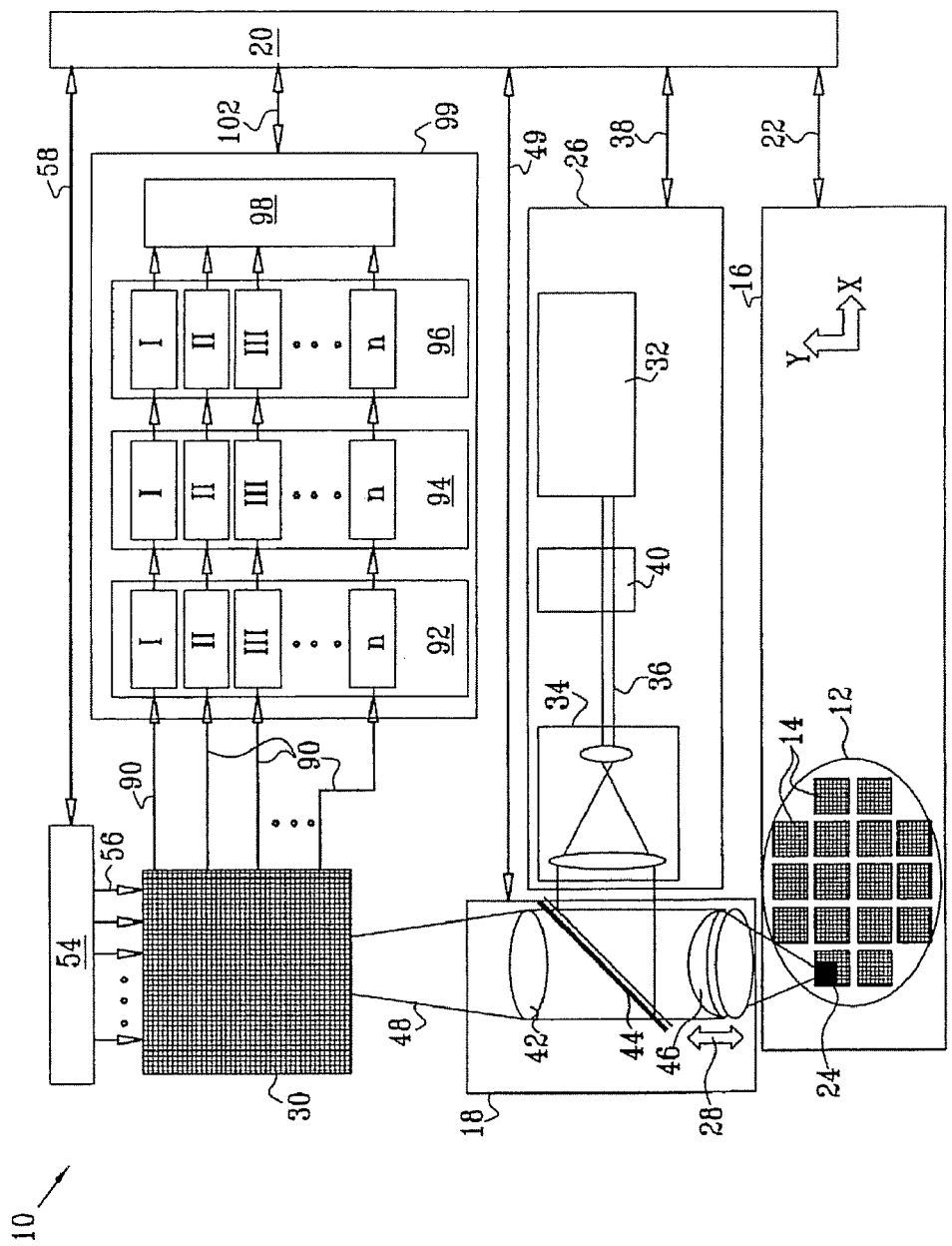
FIG. 2 is a block diagram of components in an exemplary inspection system.

A broadband illumination system 26 is provided, and can include a repetitively pulsed laser 32, a laser beam expander 34, a laser beam light path 36, and control/data links 38 as shown in FIG. 2. In some embodiments, illumination system 26 can further include one or more components that provide a spectral broadening effect as will be discussed in more detail below. This type of illumination system enables ultra fast imaging of a large field of view 24, by featuring pulsed laser 32 for repetitively generating and propagating a highly bright and highly energetic light pulse in an extremely short period of time. However, due to the spectral broadening effect, the light is not monochromatic, but rather includes a range of wavelengths. Illumination system 26 is in communication with the central control system 20 via control/data links 38.

In system 10, pulse rate, i.e., pulses per second, of pulsed laser 32 is synchronized with frame speed of the array of individual matrix photo-detectors of focal plane assembly 30. A laser pulse, illuminating field of view 24 of a wafer die 14 for a time duration of microseconds to nanoseconds (compared to milliseconds frame time of temporally gated camera system focal plane assembly 30 of matrix photo-detectors), results in instantaneous illumination of field of view 24 of an inspected wafer die 14. In one very short laser pulse, a relatively large number of pixels, for example, about forty eight million pixels, of focal plane assembly array 30 can be simultaneously illuminated, and there is essentially no relative movement among the pixels. The laser light pulse duration is preferably shorter than the image pixel dwell time or about the same order of magnitude to the pixel dwell time, where the pixel dwell time refers to the time a point on the wafer is imaged by a detector pixel while the wafer is moving.

Repetitively pulsed laser 32 may comprise a broadband laser illumination source, such as a laser sold under the trade name "Koheras SuperK Blue" by the Koheras company of Berkerod, Denmark, for example emitting illumination in the spectrum of 415 to 600 nm at a width of about 3 to 5 ns. However, pulses in the time domain may be of a duration up to, for example, 1 microsecond (us). The illumination spectrum can vary, and may comprise visible light and/or deep UV illumination. In some embodiments, the spectrum can range from about 180 to about 450 nm and may comprise any suitable sub-band or sub-bands thereof. The pulse rate of pulsed laser illumination system 26 of thirty pulses per second is synchronized with a frame speed of thirty frames per second, of the CCD matrix photo-detector(s) on focal plane assembly 30. However, other broadband illumination sources and wavelength ranges may be suitable for optical inspection purposes. Additionally, the frame speed/pulse rate may be synchronized to other values.

Some embodiments of the inspection systems discussed in the above-mentioned application Ser. No. 10/345,097 included a crystal having non-linear optical properties for use in reducing the wavelength of the illuminating laser beam. In some embodiments of the presently-disclosed subject matter, a non-linear optical element 40 may be used in addition to or instead of the crystal. In some such embodiments, non-linear optical element 40 may comprise a material having a supercontinuum effect to achieve spectral broadening. For example, the non-linear optical element 40 may comprise sub-elements, with one sub-element reducing the wavelength and another sub-element broadening the reduced-wavelength illumination.

Generally speaking, the supercontinuum effect is a non-linear effect that broadens a monochromatic or narrow-band illumination to a continuous broad-band illumination. Generally, the effect occurs when a high power laser beam is propagated through non-linear media. The broadening efficiency is dependent on factors including the optical path in the non-linear material. Therefore, in some embodiments, it is preferred to use fibers as the broadening media. For instance, rather than a broadband laser source, a high-powered monochromatic pulsed laser beam, such as the laser of some embodiments discussed in the '097 application, may be broadened using the non-linear optical element 40. For example, non-linear optical element 40 may comprise photonic crystal fibers either comprising bundle 21 or as additional components placed in the optical path before or after the bundle. In another example, a fused silica fiber, or a bundle of fused silica fibers, can be used to broaden the light spectrum. For instance, based on the non-linearity coefficients of the fused silica, fiber(s) may be selected and arranged to achieve a suitable broadening effect.

Illumination source 26 may further include one or more wavelength-dependent changeable filters in the optical path between the laser and the wafer. For instance, the filter(s) may be used to tune the illumination and/or imaging spectrum to a particular inspection application. As another example, tuning may be used for matching the spectra of different tools to ensure consistent performance. Tuning may be achieved by placing and removing one or more filters in the illumination path, for example by using a filter wheel and/or a set of rotatable polarizers for each wavelength band. Alternatively, tuning may be achieved using one or more adjustable filters and/or by adjusting the characteristics of the laser itself or the non-linear device(s) used to broaden the wavelength band. Additionally or alternatively, wavelength-dependent filter(s) may be placed in the optical path between the wafer and the imager. The specifics of tuning will be discussed in detail below.

In sub-step (b) of Step 2, an optical imaging system 18 is provided. For instance, the imaging system can include a focusing lens 42, a beam splitter 44, an objective lens 46, and control/data links 49. This system is suitable for ultra fast high resolution synchronous imaging of high magnification, for example, 50× of wide field of view 24 of one or more wafer die(s) 14. In sub-step (c) of Step 2, an automatic focusing system 28, including sensor and control devices (not shown) is provided, which, via optical imaging system 18, automatically maintains wafer 12, and therefore, wafer die(s) 14, in focus. An automatic focusing system, such as system 28, automatically adjusts and sets the position of objective lens 46 of optical imaging system 18 for optimum focus of all wafer dies 14 on wafer 12. Optical imaging system 18 is in communication with the central control system 20 via control/data links 49. During operation of wafer inspection system 10, focusing lens 42 images laser light 48, where laser light 48 represents light reflected, scattered and diffracted by wafer 12, onto focal plane assembly 30. However, the particular arrangement of the auto-focusing system can vary and is not essential to the present subject matter.

In addition or in alternative to wavelength band tuning at the illumination source, different wavelength sub-bands may be selected and filtered at the imaging system 18. For instance, one or more removable filters may be inserted into the optical path(s) in the imager to tune the detected wavelength band(s). For instance, filter wheels and/or one or more adjustable filters may be utilized as discussed in further detail below.

In sub-step (d) of Step 2, a focal plane assembly 30 is provided, including one or more detector ensembles. Each detector ensemble can feature a single or multiple two-dimensional matrix photo-detectors. For example, in some embodiments assembly 30 comprises at least one two-dimensional CCD matrix photo-detector 52 (FIGS. 3A-3B), focal plane assembly electronics 54, and control/data links 56, 58, and 90, enabling high capacity and ultra fast high resolution synchronous imaging of a wafer die 14. Focal plane assembly 30 is in communication with central control system 20 via control/data links 56 and 58 (FIG. 2).

FIGS. 3A and 3B are schematic diagrams illustrating top and side views of an exemplary two-dimensional CCD matrix photo-detector 52, respectively. In this example, photo-sensitive area 60 is surrounded by a photo-insensitive area 62, a configuration which prevents the physical placement of two CCD matrix photo-detectors side-by-side. Each two-dimensional CCD matrix photo-detector 52 can comprise any suitable type(s) of commercially available high resolution silicon two-dimensional CCD matrix photo-detectors 52, wherein each CCD matrix photo-detector 52 has a very high number of, for example, approximately two million (2 mega) or more image sensing picture elements, or pixels, capable of providing 30 frames per second at high definition standards. The detector(s) may be monochromatic or color detectors. Additionally, other types of sensors, for example CMOS sensors, may be used instead of or in addition to CCD matrix sensors. If multiple detectors are used, the detectors may be arranged into assemblies or ensembles such that a continuous surface of photosensitive areas is presented at the focal plane. For instance, FIG. 4 illustrates an exemplary arrangement of two photodetectors such that surfaces 60A and 60B are continuous at the focal plane. The continuous surface may be achieved through any suitable configuration of optical components. For example, the above-mentioned application Ser. No. 10/345,097 discusses exemplary arrangements of prisms and detectors that provide a continuous surface of twenty-four photo detectors.

Referring again to FIG. 2, in (e) of Step 2, control/data links, including 38, 49, 54, 56, and 58, and central control system 20, feature electronic interconnections among the different systems and system components, enabling proper automation and synchronization of the various steps of the method of detection of wafer defects. For example, automatic movement of wafer 12 via movement of XY translation stage 16 can be electronically set at a linear speed such that wafer 12 moves a distance of one field of view 24 between the time of two pulses emitted by pulsed laser 32 in illumination system 26. Temporally gated opening and closing, or frame speed, of focal plane assembly 30, including CCD matrix photo-detector(s) 52 is synchronized with the pulse rate of pulsed laser 32 in illumination system 26.

In Step 3, the camera system of Step 2 is adjusted, focused, and set to a position over an inspected field of view 24 within a wafer die 14, via central control system 20 signals. Pulse rate of pulsed laser 32 in illumination system 26 is synchronized with the frame speed of CCD matrix photo-detector or ensemble of detectors 52 of focal plane assembly 30. This step is performed in order to enable movement of wafer 12, and therefore, of an inspected wafer die 14, at a speed such that an inspected field of view 24 is covered during the time interval of one frame of CCD matrix photo-detectors 52 of focal plane assembly 30. In the illustration, a field of view 24 is shown within a single die. However, fields of view may comprise multiple dies, for example, when the end of one die and the beginning of the next die lie in the same field of view.

In Step 4, instantaneous illumination of an inspected field of view 24 of an inspected wafer die 14 of Step 3 is achieved by generating a laser pulse onto inspected wafer die 14, for a time duration, for example, ten nanoseconds via a central control system 20 signal. During the short laser pulse, there is effectively no wafer motion during the wafer exposure time, since the laser pulse duration is much shorter than or around the same order of magnitude as the pixel dwell time, which is the time a point on the wafer is imaged by a detector pixel while the wafer moves. Therefore, in some embodiments, there is effectively no image smear degrading image resolution, as is typically the case in wafer inspection methods and systems featuring continuous illumination of a wafer.

In Step 5, illuminated inspected field of view 24 of Step 4 is imaged by optical imaging system 18 onto focal plane assembly 30. In Step 6, the digital image (not shown) of Step 5, featuring, for example, about 48 million pixels, of an inspected field of view 24 of a wafer die 14 is acquired. This image is acquired by using focal plane assembly 30 that can, in some embodiments, optically form a continuous surface of one or more two-dimensional CCD matrix photo-detectors 52. The image is acquired via synchronized opening of temporally gated CCD matrix photo-detector(s) 52, via a central control system 20 signal. During the frame time interval of each activated CCD matrix photo-detector 52, wafer 12, and therefore, wafer die 14, moves via XY translation stage 16 the equivalent of one field of view. This corresponds to a large pixel dwell time relative to laser pulse time interval, resulting in the wafer moving only a fraction, for example, on the order of $10^{-2}$, of a single pixel during exposure to CCD matrix photo-detectors 52 of focal plane assembly 30, thereby preventing image smear or loss of image resolution. For instance, acquired digital image data can be grabbed via a set of parallel configured image processing channels 90 by an image grabber 92, and is saved in an image memory buffer 94, part of image processing system 99 (FIG. 2).

Figure 5:
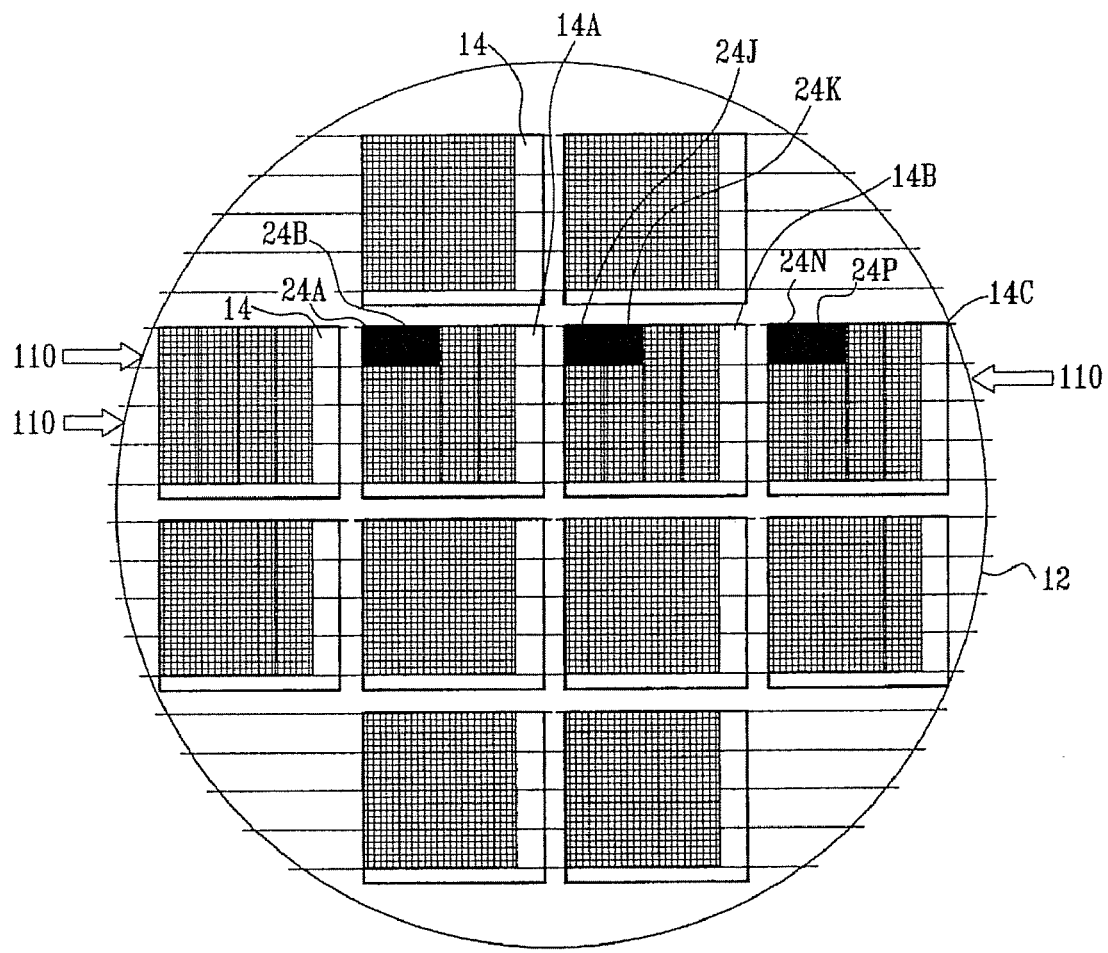
FIG. 5 is a diagram illustrating the sequential inspection of wafer dies.

In Step 7, Step 3 through Step 6 are sequentially repeated for image acquisition of the next fields of view within the same inspected wafer die 14, thereby forming a strip of fields of view. The strip may comprise fields of view from a single wafer die in some embodiments, but in other embodiments may comprise fields of view from multiple wafer dies. FIG. 5 is a schematic diagram illustrating a close-up view of the image acquisition process featuring wafer dies, where each wafer die is sequentially inspected by imaging a plurality or strips of fields of view, one field of view at a time. In FIG. 5, following image acquisition of first field of view 24A in first inspected wafer die 14A, there is image acquisition of second field of view 24B in same first inspected wafer die 14A. Synchronized with serpentine motion of wafer 12, image acquisition of successive fields of view, one after another, progresses throughout entire first inspected wafer die 14A. As was noted above, in some embodiments imaging continues until an image is acquired for fields of view in the second inspected wafer die 14B. This process results in the formation of continuous strips 110 of imaged wafer dies 14, until eventually entire wafer 12 is completely imaged.

In Step 8, a reference image or reference images corresponding to the imaged strip is obtained and/or accessed from memory. Any suitable source(s) may be used for the reference image(s). For example, the reference image(s) may comprise a median image constructed from data from other strips that were previously imaged and contain the same structural features of the inspection image strips. In other embodiments, the reference may be an image from another strip. In still other embodiments, the reference image(s) may comprise strips stitched together from a golden master image of an ideal die. The reference image(s) may be aligned with the inspection image(s) for comparison. Any suitable comparison methodology or methodologies can be used to identify potential defects and/or confirm the existence of a defect. For example, die-to-die, cell-to-cell, and/or other comparisons may be made alone or in combination.

At step 9, digital image data of each strip in an inspected wafer die and of each corresponding reference strip are processed, by using an image processing system. In FIG. 2, exemplary image processing system 99 includes parallel configured image processing channels 90 for image grabbing by an image grabber 92, an image buffer 94, a defect detection unit 96, a defect file 98, and control/data links 102. Image data acquired by focal plane assembly 30 can be processed in parallel, whereby each of multiple CCD matrix photo-detectors 52 communicates separately, in parallel to the other CCD matrix photo-detectors 52 of focal plane assembly 30, with image grabber 92, via twenty-four separate image processing channels 90. Parallel processing of acquired image data can contributes significantly to the resulting high throughput of the method of wafer inspection. In other embodiments, data from a single CCD photo-detector 52 can be broken down into components that are processed in parallel. Image processing system 99 is in communication with central control system 20 via control/data links 102.

During step 9, there is identification of the presence of one or more potential wafer defects in the inspected wafer die(s), for example, by comparing differences of pixel intensities of the image of each or any other suitable method(s). This image comparison process can be performed by software in defect detection unit 96. At step 10, each potential defect is evaluated further to determine whether or not a defect is likely at the location. For instance, the defect detection unit 96 may evaluate the area surrounding each defect candidate using one or more additional algorithms to finalize the defect determination. Confirmed wafer defect information, including location of the confirmed wafer defect, is appropriately saved in defect file 98 for possible use in feedback control of a wafer fabrication process. In Step 11, Steps 7 through 10 are repeated, sequentially, for inspection of each field of view within each strip 110 and for all strips 110 within the same wafer.

Figure 6:
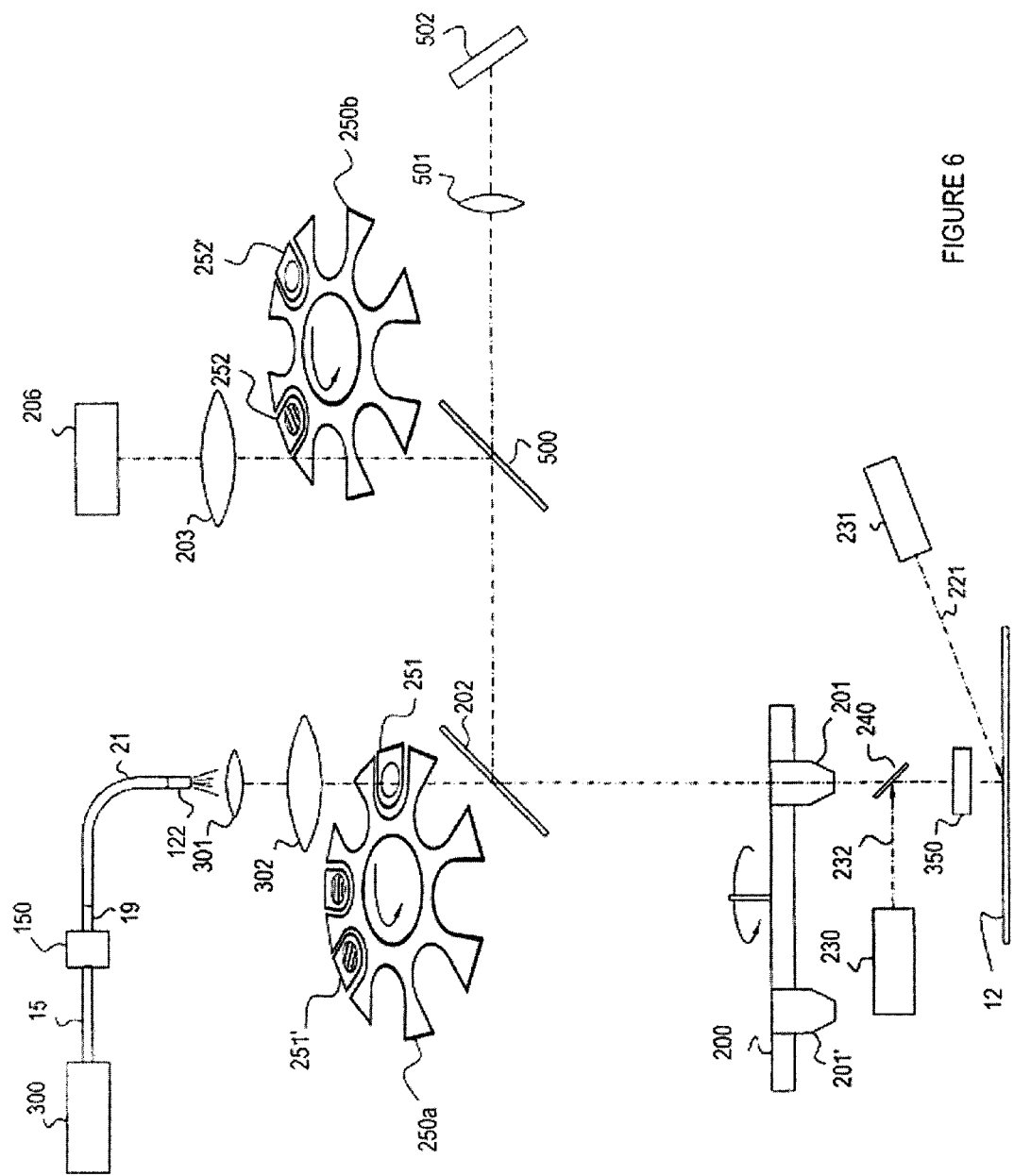
FIG. 6 is a diagram illustrating illumination and detection components in an exemplary optical inspection system.

Reference is now made to FIG. 6, which is an overall schematic side view of components in an illumination system of the defect detection apparatus, according to an exemplary embodiment of the present subject matter. According to different methods of operation, three alternative modes of illumination can be provided: Bright Field (BF), Side-illuminated Dark Field (DF) and Orthogonal or Obscured Reflectance Dark Field (ODF). Each mode of illumination is used to detect different types of defects in different production process steps. For example in order to detect an embedded defect in a transparent layer, such as silicon oxide, BF illumination is preferred. In order to detect a small particle on a surface, DF illumination generally yields better results.

In bright field illumination in general, the illumination is incident on the sample through the same objective lens as is used for viewing the sample. FIG. 6 shows a bright field illuminating laser source 300 delivering its output beam 15 into an optical delivery fiber bundle 21, preferably by means of a laser to fiber coupler 150 and terminal connector 19. This optical fiber bundle 21 provides both uniform illumination on the sample and coherence breaking of the laser illumination. In some embodiments, only a single fiber bundle is used, but it is to be understood that a serial fiber bundle solution may also be suitable. In other embodiments, one or more bundles may be combined with further components, such as a light guide or guides. Discussion of exemplary fiber/light guide combinations can be found in co-pending U.S. patent application entitled "Speckle Reduction Using a Fiber Bundle and Light Guide," Ser. No. 11/503,859, filed Aug. 14, 2006, and incorporated by reference herein for all purposes. Bundle or bundles 21 may comprise one or more materials having a super-continuum effect that provide for spectral broadening of the beam output from laser source 300.

From the output termination 122 of the fiber bundle 21, the laser beam is imaged by means of illumination transfer lenses 301, 302 onto the objective lens in use 201, which is operative to focus the illumination onto a wafer 12 being inspected. Appropriate alternative objective lenses 201' can be swung into place on an objective revolver 200, as is known in the microscope arts. The illumination returned from the wafer is collected by the same objective lens 201, and is deflected from the illumination path by means of a beam splitter 202, towards a second beam splitter 500, from where it is reflected through the imaging lens 203, which images the light from the wafer onto the detector 206. The second beam splitter 500 is used to separate the light going to the imaging functionality from the light used in the auto-focus functionality, which is directed by means of the auto-focus imaging lens 501 to the auto-focus detector 502.

When conventional dark field illumination is required for the imaging in hand, a dark field side illumination source 231 is used to project the required illumination beam 221 onto the wafer 12. When orthogonal dark field, or obscured reflectance dark field illumination is required for the imaging in hand, an alternative dark field illumination source 230 is used to project the required illumination beam 232 via the obscured reflectance mirror 240 onto the wafer 12 orthogonally from above. FIG. 6 indicates sources 300, 231, and 230 at different locations. However, any or all of sources 300, 230, and 231 may comprise the same light source, with the bright field, dark field, and obscured reflectance dark field effects achieved through moving the source(s) and/or redirecting illumination to the appropriate angle using one or more optical components.

FIG. 6 shows variable focusing element 350, which, as detailed below, may be used to selectively focus certain wavelength bands or sub-bands at various locations relative to the wafer surface. In FIG. 6, focusing element 350 is shown as a dispersive window placed between the objective and the wafer. However, focusing element 350 may be selectively placed in the optical path at any suitable point and in any suitable fashion. In some embodiments, the wavelength-variable focusing provided by element 350 can be provided by one or more objective lenses 201 included in revolver 200.

FIG. 6 additionally shows two exemplary filter wheels, 250a and 250b, which each comprise a plurality of filters, including filters 251 and 251' and filters 252 and 252', respectively. One or more of the filter wheels 250 can be rotated to selectably place spectral and other filters in the illumination path. The filter(s) can be used to tune the illumination spectrum of the light illuminating the wafer and/or the light returned from the wafer. Although the filter wheels 250 and 250a are depicted differently in FIG. 6 than objective revolver, this is for purposes of illustration only and in practice the wheels and revolver may be of similar or different construction.

In FIG. 6, a filter wheel 250a is positioned in the illumination path between transfer lens 302 and beam splitter 202 for tuning the spectrum of the illuminating light during bright field illumination. A second filter wheel 250b is placed in the imaging path between beam splitter 500 and detector 206. Thus, filters such as 251 and 251' in this example can be used to selectively filter bright-field illumination, while filters such as 252 and 252' in second wheel 250b can be used for filtering the light returning from the wafer for any illumination. In some circumstances, the filter wheels may include "blank" areas where a transmissive window or no filter are present. An example of this is shown in FIG. 6, where filter wheel 250b is positioned so that there is no filter in the optical path. For instance, during bright-field illumination, wheel 250b may be adjusted so that illumination is not filtered multiple times. However, assuming filters 252 and 252' comprise Fourier filters as discussed later in this disclosure, then during dark-field illumination wheel 250b may be used to selectively place one or more of the Fourier filters in the optical path. Fourier (and other) filters may, of course, be used in bright field or other illumination modes, as well.

In some embodiments, a filter wheel or other filter(s) may be placed at other points in the optical path. For example, a filter wheel or other filter(s) could be positioned in the optical path between beam splitter 202 and detector 206 for purposes of filtering light prior to detection but not during illumination from laser 300. Similarly, in embodiments in which sources 230 and/or 231 comprise separate illumination sources, a filter wheel or other filter arrangements may be included in the path between the source(s) and the wafer. For example, a filter wheel could be positioned in the path between source 231 and the wafer to selectively filter dark-field illumination.

Although filter wheels 250 are shown, filters such as 251, 251', 252, and 252' may be placed at various locations in the optical path in any suitable fashion. For instance, filters may be positioned using other components such as conveyors, robotic arms, and the like whereby the filter(s) can be selectively moved in and out of the optical path. Additionally, some filters may be placed manually into the optical path. For instance, for purposes of tool matching, one or more filters may be inserted into the optical path near the illumination source(s). Once tools have been matched, generally speaking, there will be little to no need to spectrally adjust the filters used for matching. Therefore, those filters may comprise fixed filters. Of course, "fixed" is meant in the relative sense as compared to selectable filters; a "fixed" filter does not need to be irreversibly installed.

In this example, different filter characteristics are selected through placement and removal of filters with differing characteristics into the optical path, such as by choosing from filters 251 and 251'. However, in some embodiments, filters such as 251 and 251' may comprise tunable filters whose characteristics can be adjusted in-place. Generally, the filters are selected (and/or filter characteristics adjusted) in order to select certain wavelength bands or sub-bands for use in the inspection process.

The nature of a laser beam, and especially its coherent nature, presents a number of problems when used as an illuminating source in applications requiring a uniform illuminating flux over the inspected area, such as is required, for instance, in a wafer inspection system, and such problems have been discussed in prior applications such as the aforementioned Ser. No. 10/345,097.

In order to overcome such problems, various coherence breaking schemes have been developed. For instance, speckle effects with CW lasers are comparatively easy to overcome, since it is possible to average the signal while varying the wave front. Several methods are described in the prior art for achieving this. When, however, the imaging process utilizes a single narrowband pulse for each acquired image, such a method becomes difficult to implement. However, the use of broadband illumination may in itself reduce speckle noise.

According to further embodiments, there are provided methods whereby the coherence effect of the laser beam may be further reduced by splitting the laser beam into many beamlets and retarding each beamlet relative to the previous one in such a way that there is no definitive phase difference between them. The laser beam is thus divided into many parts, each part having no defined phase coherence with the other parts. This requirement is insufficient, however, since it is also required that each point in the field of view (FOV) on the sample is illuminated by all parts of the laser beam. Each part of the beam is coherent or partially coherent with itself and thus may contribute to the generation of speckle, or to other interference effects that create high contrast artifacts in the image. Since each part of the beam is not coherent with the other parts of the beam, by ensuring that the FOV is illuminated by all parts of the laser beam, the total effect is averaged. The residual coherence effect depends on the number of beamlets used. Since each beamlet is independent of the others, the interference effect is reduced by the square root of the number of beamlets, assuming that all beamlets have the same intensity contribution. Consequently, the greater the number of beamlets, the lower the level of appearance of coherence artifacts in the image.

Figure 7:
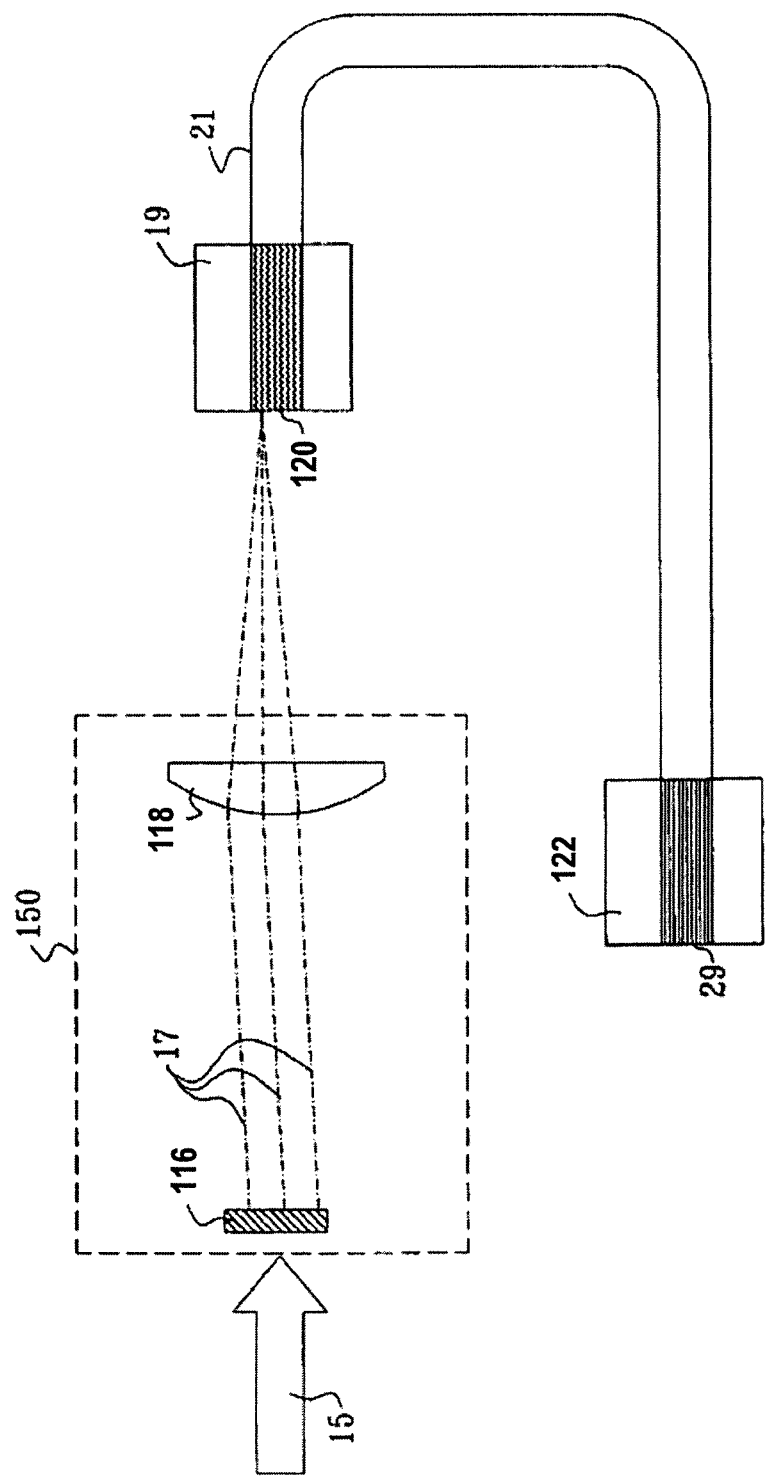
FIG. 7 is diagram of an exemplary fiber optic illumination system suitable for use in an optical inspection system.

In some embodiments implementing this technique, the laser beam is introduced into a fiber optics bundle, such as the fiber bundle 21 shown schematically in FIG. 7. The fibers in the bundle differ in length from each other by distances of the order of the laser coherence length in the fiber medium. For example, the differences may be more than, less than, or equal to the laser coherence length. The number of fibers in the bundle dictates the contrast of the residual coherence effect in the image. The fiber bundle should preferably be illuminated uniformly. Each fiber in the bundle must carry more or less the same energy; otherwise averaging of the coherence effect will not be efficiently performed. Since the laser beam itself is not uniform and contains high and low spatial frequency components, the laser beam must be spatially mixed before introduction into the fiber. Additionally, the full numerical aperture of the fiber should preferably be filled, since at the far end of the bundle, uniform angular distribution of intensity is required.

Fiber bundle 21 may comprise photonic crystal fibers which provide the spectral broadening effects. For instance, some fibers in one or more bundles, or one or more entire bundles, may comprise photonic crystal fibers. The bundles of photonic crystal fibers may be used in addition to or instead of bundles of other fibers. Fiber bundles may be arranged in sequence to one another and/or may be used in conjunction with other components to reduce any lingering problems due to the coherency of the illumination source. In some embodiments, instead of photonic crystal fibers, other fibers that broaden the light can be used.

Fourier filtering is used in some embodiments to filter out pattern information in order to better detect small defects and anomalies hidden in the image of a multiply repetitive region of a pattern covering a wafer. However, the use of broadband illumination introduces additional considerations that are addressed by the present subject matter in order to provide for an efficient and effective inspection.

Referring still to FIG. 7, the laser beam 15, which can be either a parallel beam or slightly convergent, or slightly divergent impinges onto a diffusing element 116 which, according to alternative and preferred embodiments, can be a regular diffuser, a holographic diffuser (such as an MEMS) or a micro-lens array having a numerical aperture that spreads the incident light at the required angles. The diffused beam, shown schematically in FIG. 7 by means of three exemplary rays 17 diffused at the same angle from different locations in the diffuser, is preferably imaged onto one point of the end face 120 of the terminal connector 19 of a fiber optics bundle 21 by means of a focusing element 118, which can be either a single lens, or, in order to reduce aberrations, a multi-element lens. Rays diffused at different angles from those 17 shown in FIG. 7, are imaged onto different points of the end face 120 of the fiber optics bundle 21. Light from all of the included angles at which light is output from the diffuser is thus imaged by means of the focusing element 118 to cover the entire input aperture of the fiber bundle end face 120. The beam traverses the fiber bundle 21 and is output at the opposite end face 29 of the fibers at the output connector 122.

The geometry on a semiconductor wafer generally includes a large-scale multiply repetitive pattern defined by the dies of the wafer. Within each die, there are often areas in which there appears an array of a repetitive pattern with a cycle of a few microns. This occurs especially in memory chips or in the memory area in a logic chip. When coherent or partial coherent illumination is incident on such a periodic array, the array serves as a diffraction grating that reflects the light only in the defined Bragg angles. The reflected light produces a diffraction pattern of spots in the back focal plane of the objective lens. This plane is also referred as the Fourier plane of the lens, since the image obtained in this plane is a two-dimensional Fourier transform of the object. The smaller the cycle in the object plane, the larger the distance between the spots in the Fourier plane. The size of these spots depends on the optical quality of the objective lens, but even more on the nature of the incident light. When the input light is a collimated beam, the spot size is very small. In U.S. Pat. No. 5,970,168 to Montesanto et al., for "Fourier Filtering Mechanism for Inspecting Wafers" there is described the use of a spring array as a Fourier plane filter, with a built-in damping mechanism to prevent interference from mechanical vibrations.

According to some embodiments of the present subject matter, an extended source, which need be only partially coherent and may be the same as used in dark field side illumination, is used to produce defined spots in the Fourier plane. According to this method, when the illuminating beam is such an extended light source, the size and shape of each of the spots in the Fourier plane becomes a miniature image of the extended source. Furthermore, in order to produce the diffraction pattern in the Fourier plane, it is not necessary that each point in the extended source be a coherent source. This extended and partially coherent form of illumination is successful in generating a Fourier plane diffraction pattern array, because each separate area of the illuminating beam is made up of an assembly of self coherent spots, but unrelated to each other. This is an outcome of the optical treatment performed on the illuminating beam by means of the imaging optics for the fiber optical output.

Generally speaking, if the structural periodic information from the image can be filtered out, the optical information anomalies resulting from defects on the wafer can be revealed in the form of non-periodic information spread over a wide range of spatial frequencies. This is performed in practice by blocking the transmission of light specifically in the area of those spots, eliminating the information relevant to the repetitive pattern from the image from the remaining optical information transmitted past the Fourier plane, thus making it easier in some cases to detect anomalies caused by departures from the desired pattern on the wafer. However, if too much of the plane is masked, then the image quality may be degraded.

Figure 8:
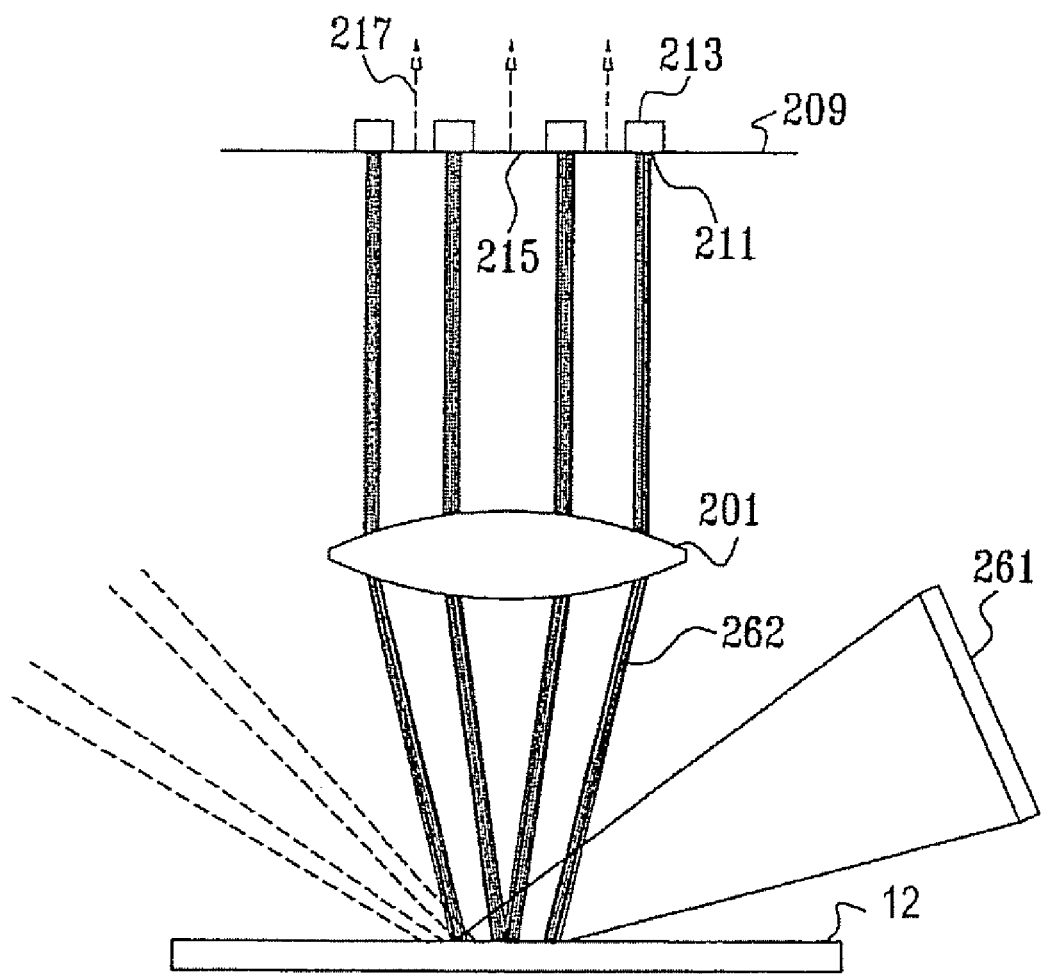
FIG. 8 is a diagram illustrating the principles of Fourier filtering in optical inspection systems.

Reference is now made to FIG. 8, which schematically illustrates an exemplary method for performing this procedure. An extended source 261, which can even be non-parallel, as preferably used in dark field side illumination, is incident on the wafer 12 under inspection. The scattered light 262 from the wafer features is imaged by the objective lens 201. At the back focal plane 209 of this lens, which is the above-mentioned Fourier plane, there is generated a patterned array of spots 211 representing the repetitive features of the wafer being imaged by the scattered light. In the interstitial positions 215 between these spots, there may appear any light scattered from non-repetitive features on the wafer die, such as from a defect which it is desired to detect. A mask 213, constructed to exactly block the light from the predetermined patterned array of spots 211, is disposed at the Fourier plane, thus allowing scattered light 217 from defects present on the wafer die to pass the Fourier plane, and to be imaged and detected by the system, without interference from the expected repetitive features of the wafer die.

However, the use of broadband illumination, as noted above, introduces additional complications. As noted above, illumination generally produces a spot or an array of spots. However, the density of the image (i.e. the distribution of spots) varies with wavelength. For instance, shorter wavelengths produce denser images. Broadband illumination comprises a continuous wavelength band. Thus, the image(s) formed by repetitive features at the Fourier plane will have some aspects that are predominately due to certain wavelength sub-bands of the illumination and other aspects that are predominately due to other wavelength sub-bands of the illumination. Some of the spots may overlap and some spots may be widely distributed from other spots. Therefore, in order to filter repetitive patterns out, the Fourier plane can be masked at multiple locations. However, as noted above, too much masking may degrade the image by blocking light not related to the repetitive aspects. Therefore, as noted below, masking each band in a different area can advantageously reduce the masked area.

Figure 9A:
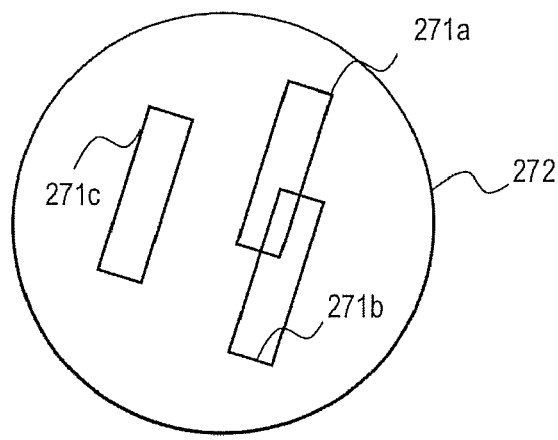
FIGS. 9A and 9B illustrate exemplary Fourier filtering methodologies for use in optical inspection systems featuring broadband illumination.
Figure 9B:
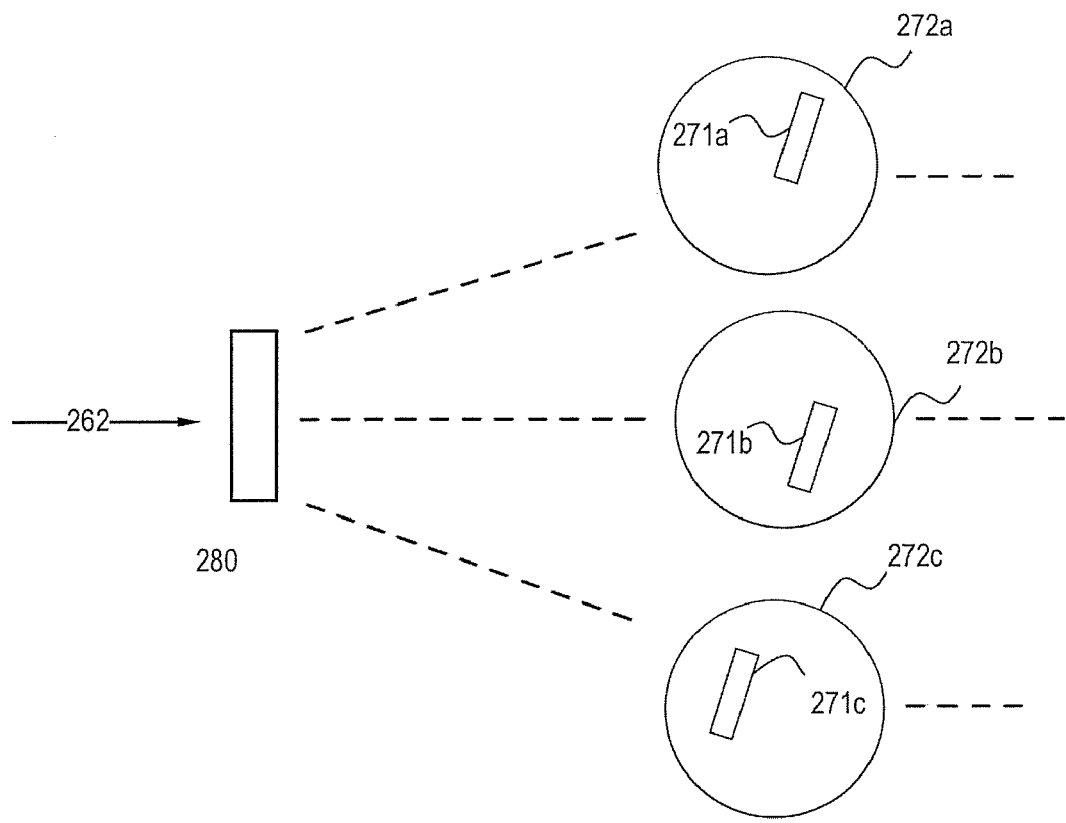

FIGS. 9A and 9B illustrate different embodiments of a Fourier filtering approach suitable for broadband inspection applications, though, of course, the approaches could be combined. In FIG. 9A, a filter mask 272 is provided. Filter mask 272 features a plurality of blocking areas or elements 271a, 271b, and 271c. Although each area comprises a single component in this example, any area could comprise multiple portions, and a filter can include more or fewer different areas than are discussed in these examples. The different areas may overlap to varying degrees. Generally speaking, the size, shape, and arrangement of the areas and the actual patterns within the areas will depend on the particular wafers, the particular wavelength sub-bands in question, and the particular illumination method.

Filter mask 272 may be constructed of any suitable materials, including glass, plastic, or other transparent material, with blocking areas 271 comprising material disposed in or on the mask to block light. Alternatively, filter mask 272 may comprise an array of moveable elements, a modifiable array (such as a MEMS array or LCD array) or otherwise as discussed in application Ser. No. 10/345,097. Examples of the construction of Fourier filters by printing can be found in co-pending application Ser. No. 11/410,276, filed Apr. 24, 2006, which is hereby incorporated by reference herein for all purposes.

However, in the presently-disclosed embodiments, each respective blocking area 271 is configured to block information related to repetitive patterns at a particular wavelength sub-band of the broadband illumination. For instance, for a spectrum of 200-350 nm, area 271a may be configured to block light at the sub-band 200-250 nm, area 271b may be configured to block light at sub-band 250-300 nm, and area 271c may be configured to block light at sub-band 300-350 nm. In FIG. 9A, areas 271a through 271c are provided in a single filter 272. For example, each area 217a through 271c may comprise a separate layer of filter 272, for instance, which is fabricated using different optical coatings for each layer. In such embodiments, the coatings could be selected such that the particular band is blocked but other bands are not significantly attenuated.

FIG. 9B shows an alternative approach. In FIG. 9B, the wafer image has been split into multiple wavelength sub-bands. For example, an imager may include one or more splitting elements 280 such as dichroic elements that split the scattered light 262 from the wafer 12 into separate wavelength sub-bands. For instance, continuing with the example from above, the image may be split into a 200-250 nm band, a 250 to 300 nm band, and a 300 to 350 nm band. The bands may overlap to a greater degree in some embodiments. Three separate filter masks, each corresponding to a wavelength sub-band, may then be constructed. In this example, filter 272a includes blocking area 271a, filter 272b includes blocking area 271b, and filter 272c includes blocking area 271c. Then, the three separate filter masks 272a, 272b, and 273c are inserted into the respective optical paths. The separate sub-bands may then be combined after filtering into a single image by additional elements (not shown in FIG. 9B).

In order to design one or more filter masks, it is useful to view the image obtained in the Fourier plane. For example, to design a mask for a particular layer, that layer may be imaged. Usually the Fourier plane is the back focal plane of the objective. However, if the back focal plane is inaccessible, as with many high power objective designs, an image of the back focal plane may also be used. Similarly, placement of Fourier filters can occur at any Fourier plane(s).

Figure 10:
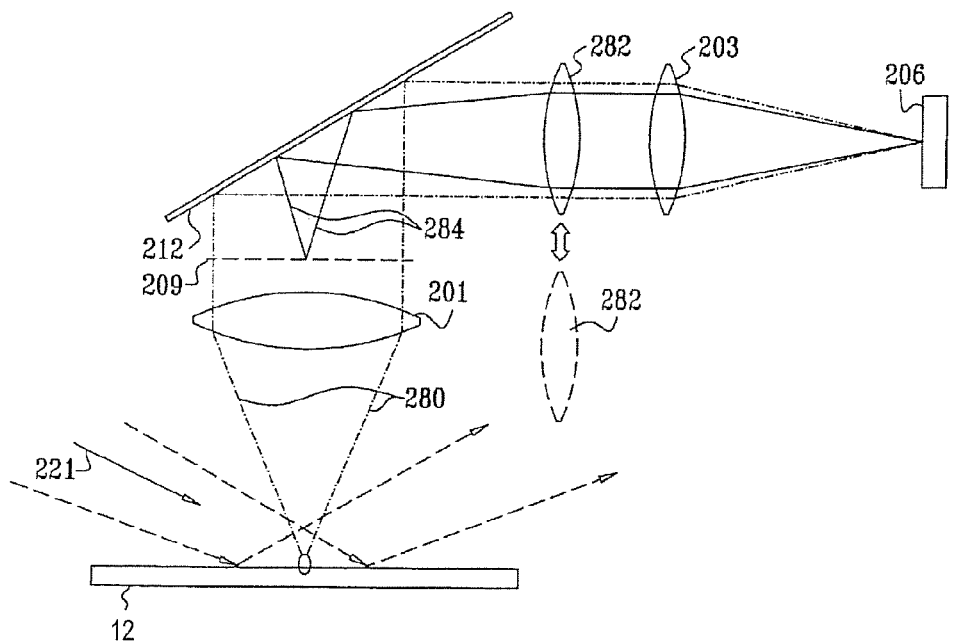
FIG. 10 is a diagram illustrating an exemplary method for obtaining a Fourier image.

Reference is now made to FIG. 10, which illustrates a method, in another exemplary embodiment, by which this plane can be imaged onto the existing detector by introducing an additional lens (or group of lenses) into the imaging optics. In the embodiment of FIG. 10, dark field side illumination 221 is incident on the wafer 12, and the scattered light, as designated by the dashed lines 280, is collected by the objective lens 201, for imaging on the detector 206 by means of the detector imaging lens 203, all as previously described hereinabove.

The Fourier plane 209 is located behind the objective lens 201, and may be in a position where it is not easy to locate a detector for direct imaging. Therefore, when the Fourier plane has to be viewed in order to determine the correct Fourier plane filter to construct, an additional imaging lens 282, known as the Fourier imaging lens, is inserted into the imaging path, increasing the power of the detector imaging system, such that the detector now images the Fourier plane 209. The solid lines 284 in FIG. 10 represent the optical imaging path from the Fourier plane to the detector, with the Fourier imaging lens in position. In this manner, the exact required pattern of the spatial filter in the Fourier plane for a specific die region can be designed according to the imaged field of the object.

The illumination source can be tuned or filtered so that repetitive elements for a specific wavelength sub-band are imaged in sequence. For example, to determine the location of blocking areas 271a from FIGS. 9A-B, the illumination source may be tuned or filtered such that only light from 200-250 nm is used. Depending on the implementation of the inspection system, the illumination source may be tuned to emit 200-250 nm illumination. For instance, the illumination may be filtered such that only 200-250 nm illumination is incident on the wafer and/or light from the wafer may be filtered to pass only 200-250 nm light to the detector. The filters/tuning may then be changed in order to determine the location of blocking areas 271b and 271c for their respective wavelength sub-bands. The Fourier filter mask(s) can then be implemented either by control over one or more reconfigurable spatial filters, such as an LCD or other configurable spatial filter(s), or the output used to construct one or more fixed filters. As was mentioned above, fixed filters can be constructed in any suitable manner, including by printing one or more layers such as is described in application Ser. No. 11/410,276.

The filter mask(s) can be placed into and removed from the optical path in any suitable manner. For instance, one or more filter wheels 250 may be provided for selectably placing filters into the optical path between the wafer and the detector (s). In some embodiments, the filters are carried by a separate filter wheel from selectable filters used in tuning the illumination spectrum. For example, FIG. 6 shows filter wheel 250b carrying masks such as 252 and 252'. Some or all of the filters included in wheel 250b may comprise Fourier filters, with the wheel positioned so that the Fourier filters can be selectively moved into a Fourier plane. However, as noted above, the filters may be placed in the optical path in any suitable fashion, including robot arms, servo controls, and the like, or even manually. If multiple Fourier filters are used in accordance with FIG. 9B, then the splitting element(s), filters, and recombination element(s) may be located in the imaging path so that each filter is located at a Fourier plane.

Figure 11A:
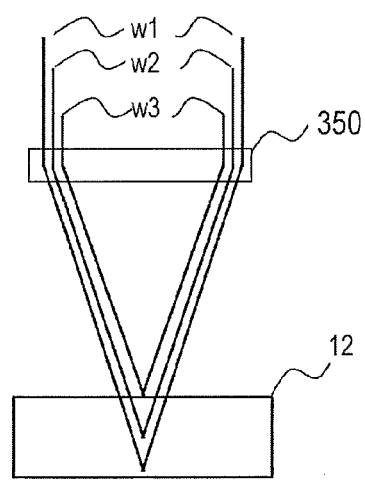
FIGS. 11A-B illustrate an exemplary focusing arrangement for use in an optical inspection system featuring broadband illumination.
Figure 11B:
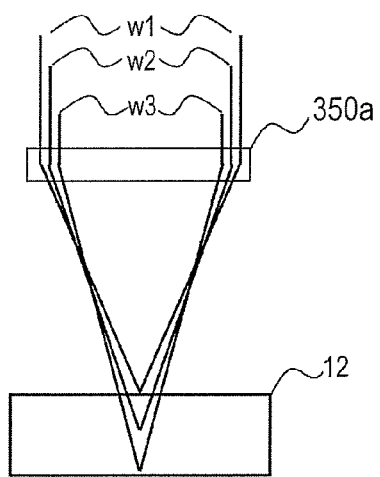
Figure 12:
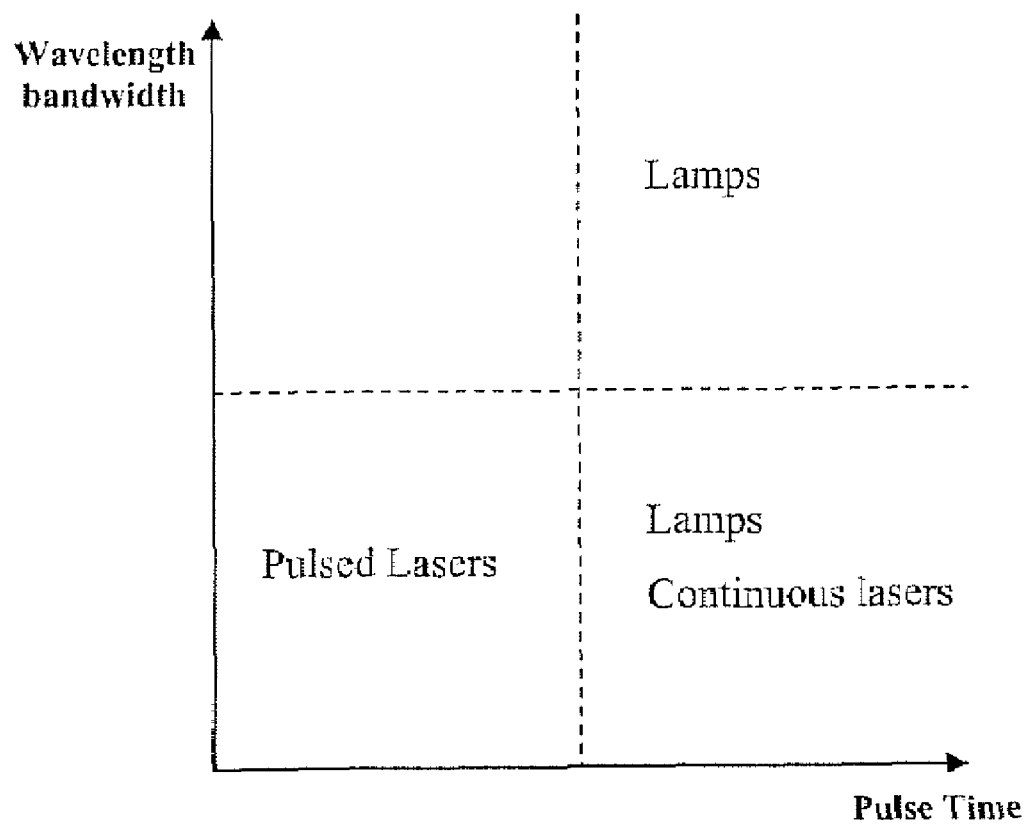
FIG. 12 is a graph generally depicting the time-domain and wavelength-domain characteristics of various exemplary illumination sources.

FIGS. 11A and 11B illustrate additional components that may be used to enhance inspections that utilize broadband illumination. FIGS. 11A and 11B illustrate variable focusing elements 350 and 350a in which each represents one or more optical elements that are configured to adjust the focus of different wavelength sub-bands relative to the wafer 12. For instance, element 350 may comprise a dispersive window, an objective lens, another lens or other suitable optical element(s). In some circumstances, certain wavelength sub-bands may be focused below the wafer surface while other sub-bands are focused on the surface and still further sub-bands are focused above the surface. The lines w1, w2, and w3 illustrate the paths taken by different exemplary wavelength bands. In FIG. 11A, variable focusing element 350 is shown focusing wavelength sub-bands differently than those sub-bands that are focused by variable focusing element 350a in FIG. 11B. Variable focusing element 350a may represent an additional component that is inserted into the optical path or a reorientation or adjustment of element 350. Depending on the type of defect that is to be detected or other inspection needs, the focusing location of the wavelength bands may be varied. For example, if the inspection seeks detection of sub-surface defects, the multiple wavelength sub-bands may be focused at the sub-layer to achieve broadband illumination at that layer.

Selection and/or adjustment of elements for wavelength-dependent focusing may be part of a larger tuning and calibration process that may be implemented for inspection using broadband illumination. In contrast to monochromatic systems, inspection systems that support broadband illumination introduce additional variables into the inspection process that must be addressed. For instance, as noted above, Fourier filtering components and methods may need to address the implications of multiple wavelength sub-bands. However, the overall inspection process can benefit from tuning and calibration whereby certain wavelength sub-bands are selected for particular inspection operations. For instance, wavelength bands and sub-bands may be selected for operations including recipe tuning, in-process tuning, and tool matching.

For example, a particular wafer 12 that is being inspected may include one or more areas of different degrees of color variation. Generally, the inspection resolution is proportional to the wavelength that is used—that is, smaller wavelengths allow for finer inspection. On the other hand, color variation can be addressed through use of broadband illumination. Accordingly, as part of the inspection process, the inspection tool can be tuned, either for a particular recipe or in real-time (or near real-time) as inspections occur, in order to determine the best wavelength band(s) for use in inspection by weighing factors such as the desired resolution to acceptable amount of color variation.

For example, when preparing a recipe that includes parameters governing the inspection process for a particular wafer or batch of wafers, different areas of the wafer can be evaluated for color variation. For instance, a periphery area on a wafer die may be subject to greater color variation than, say, a memory array area. Depending on the amount of color variation, the inspection system can be tuned to use varying degrees of broadband illumination. The inspection recipe may specify that the periphery area is to be inspected using a wider band of illumination than the memory array area.

Wavelength band and sub-band selection may occur during the inspection process. For instance, the illumination spectrum may be adjusted in real time or near-real time based on evaluating the degree of color variation and/or other inspection feedback (in addition to or instead of the recipe). For example, if inspection of an area initially proceeds using broadband illumination but a high number of defects are detected, the illumination band may be adjusted to be narrower to allow for higher resolution.

The illumination bands may be selected using any suitable combination of tuning and filtering. For example, as noted above, the illumination source may comprise a broadband laser or a laser optically linked to one or more components that provide a spectral broadening effect. The laser and/or components may be tunable such that particular wavelength bands and sub-bands can be selected. Tuning of the source may also be accomplished by substituting different non-linear elements and/or substituting different lasers.

Additionally or alternatively, one or more filters can be placed after the illumination source. For example, one or more filters may be placed in the illumination path between the source and the wafer and/or in the imaging path between the wafer and the imager. The filter(s) may themselves be tunable to block and pass different wavelength bands. As an example, one or more tunable filters may comprise wavelength separating components such as a prism or grating, an attenuation or switching grid such as a MEMS-based device, and/or LCD-based devices in which each pixel in the grid affects a different portion of the wavelength spectrum. Alternatively or additionally, the filters may have fixed characteristics such that the filters are configured to block and pass specified wavelengths, with the inspection tool configured to place and remove the filters as part of the tuning process.

For instance, the filters may be placed in and removed from the path using robotic arms, conveyors, and other devices. As another example, a filter wheel or wheels may be placed such that filters can be selectably placed and removed from the optical path. Continuing with the example above, filter 251 of FIG. 6 may allow a wide band of illumination to pass, while filter 251' reduces the bandwidth to more closely resemble narrowband illumination. Thus, when greater resolution is desired, filter wheel 250 may be rotated to place filter 251' in the optical path.

Tool matching may also require tuning of the broadband illumination. For example, due to inconsistencies between the lasers and/or other optical components, the spectral broadening effects may not be the same between any two given inspection tools. Accordingly, in order to obtain consistent inspection results between tools, the illumination spectra can be adjusted so that the illumination spectrum is identical or as close as is possible between tools. The adjustment may be made at the time the tool is assembled and/or when multiple tools are to be used in conjunction with one another.

For example, if a first tool and a second tool are to be used alongside one another, the unfiltered illumination spectra for both tools may be measured. Then, the spectrum difference between the tools may be determined and the tools matched by inserting one or more filters in the illumination path. For instance, if the first tool provides a broader illumination spectrum than the second tool, then the first tool's spectrum may be reduced by a filter placed just after the first tool's illumination source. The filters may comprise fixed or changeable filters. For instance, one or more filter wheels, tunable filters, or other components may be included in the tool for selective placement in the optical path for tuning purposes. Additionally, other optical components included in the tool may be adjusted to reduce or avoid spectrum variance between tools. For example, if other optical components in one of the tools (e.g. transfer lenses, beam splitters, etc.) do not have the same characteristics across the broadband spectrum, then additional tuning filters may be included to account for such effects.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art. Additionally, the discussion of and/or incorporation by reference of certain materials is not intended to act as an admission of any sort that such materials are, or are not, prior art.

What is claimed:

1. A wafer inspection system comprising:
   a. an imager operative to image at least one wafer while the wafer is illuminated and to determine a plurality of spectra for a plurality of regions of the wafer based on data including a degree of color variation in first and second regions of the wafer, the imager including at least one detector;
   b. an illumination source comprising a laser and a non-linear optical component having a spectral broadening effect on light from the laser, so that the illumination source is configured to illuminate the at least one wafer with a pulse of illumination no longer than 1 ps in time and having a continuous spectral range of at least 20 nm; and
   c. tuning means disposed in an optical path between the illumination source and the imager, the tuning means operative to tune a spectrum of the wafer inspection system to a desired spectrum by adjusting the spectrum to at least a first spectrum for inspection of the first region of the wafer and adjusting the spectrum to a second spectrum for inspection of the second region of the wafer.

2. The inspection system as set forth in claim 1, wherein the illumination source comprises a pulsed laser configured to emit illumination having a spectral range falling within a range of 180 to 450 nm.

3. The inspection system as set forth in claim 1, wherein the non-linear optical component comprises one or more photonic crystal fibers.

4. The inspection system as set forth in claim 1, wherein the non-linear optical component comprises one or more fused silica fibers.

5. The inspection system as set forth in claim 3, wherein the non-linear optical component comprises a bundle of photonic crystal fibers, at least some of the fibers in the bundle having differing optical lengths from one another.

6. The inspection system as set forth in claim 1, wherein the tuning means comprises at least one filter;
   a. wherein the filter is configured to pass one or more specified ranges of wavelengths;
   b. wherein the at least one filter is placed in the imaging path between the wafer and the at least one detector so as to filter light traveling from the wafer before said light reaches the detector.

7. The inspection system as set forth in claim 1, wherein the tuning means comprises at least one filter;
   a. wherein the filter is configured to pass one or more specified ranges of wavelengths;
   b. wherein the at least one filter is placed in the illumination path between the illumination source and the wafer so as to filter light traveling from the illumination source before said light reaches the wafer.

8. The inspection system as set forth in claim 1, further comprising:
   a. at least one optical element positioned to form an image of the wafer, the optical element having a Fourier plane; and
   b. at least one filter mask placed in the Fourier plane;
   c. wherein the at least one mask is configured to block light corresponding to repetitive features of the wafer under inspection, the light falling in a continuous wavelength band.

9. The inspection system as set forth in claim 8,
   a. wherein at least one filter mask comprises a plurality of blocking areas; and
   b. wherein at least some of the blocking areas block light in different wavelength sub-bands within the continuous wavelength band than the other blocking areas.

10. The system as set forth in claim 8,
    a. wherein the system comprises a plurality of filter masks; and
    b. wherein at least some of the masks are configured to block light in different wavelength sub-bands within the continuous wavelength band than the other masks.

11. The inspection system set forth in claim 1, further comprising at least one optical element configured to focus at least one wavelength band of the illumination source at a different point above or below a focus point of another wavelength band relative to a surface of the wafer.

12. The inspection system as set forth in claim 11, wherein the system includes a plurality of optical elements configured to be selectively inserted into the optical path to adjust the dependency of the focus on wavelength.

13. A method of inspecting a wafer in an optical inspection system, the method comprising:
    a. emitting a pulse of light, the pulse no longer than 1 ps in time;
    b. directing the emitted pulse into a nonlinear optical element to obtain broadband illumination having a continuous spectral range of at least 20 nm;
    c. directing the broadband illumination toward the wafer;
    d. capturing at least one image of at least a portion of the wafer using an imager comprising at least one detector;
    e. determining a plurality of spectra for a plurality of regions of the wafer based on data including a degree of color variation in first and second regions of the wafer; and
    f. tuning a spectrum of the inspection system to a desired spectrum by adjusting the spectrum to at least a first spectrum for inspection of the first region of the wafer and adjusting the spectrum to a second spectrum for inspection of the second region of the wafer in order to reduce the color variation in images of the first and second regions.

14. The method as set forth in claim 13, wherein the non-linear optical element comprises a bundle of photonic crystal fibers.

15. The method as set forth in claim 14, wherein at least some of the fibers in the bundle have differing optical lengths from one another.

16. The method as set forth in claim 13, wherein directing the broadband illumination includes focusing an illuminating beam such that at least one wavelength band of the beam is focused at a different location above or below a focus point of another wavelength band of the beam relative to a surface of the wafer.

17. The method as set forth in claim 13, wherein tuning includes filtering light by placing at least one filter in an optical path between the nonlinear optical element and the wafer.

18. The method as set forth in claim 13, wherein tuning includes filtering light by placing at least one filter in an optical path between the wafer and at least one detector included in the imager.

19. A method comprising:
    a. illuminating a wafer with broadband illumination, wherein the wafer includes at least some repetitive structural features;
    b. collecting illumination returned from the wafer by using at least one optical element having a Fourier plane and splitting the illumination returned from the wafer into a plurality of wavelength sub-bands, each wavelength sub-band having a separate optical path;
    c. placing at least one filter mask at the Fourier plane in each optical path, wherein the at least one filter mask in each optical path is configured to block light containing information related to the repetitive features at a plurality of the respective optical path's wavelength sub-band;
    d. tuning a spectrum of the broadband illumination to a desired spectrum for each of a plurality of regions of the wafer by adjusting the spectrum according to color variations between images of the plurality of regions of the wafer.

20. The system set forth in claim 1, wherein the pulse of illumination has a length of at least 1 ns in time.

21. The system set forth in claim 1, wherein the pulse of illumination has a continuous spectral range of at least 50 nm.

22. The method set forth in claim 18, wherein the pulse of illumination has a length of at least 1 ns in time.

23. The method set forth in claim 13, wherein the pulse of illumination has a continuous spectral range of at least 50 nm.

24. A wafer inspection system comprising:
    a. an imager operative to image at least one wafer while the wafer is illuminated and to determine a plurality of spectra for a plurality of regions of the wafer based on data including a degree of color variation in first and second regions of the wafer, the imager including at least one detector;
    b. an illumination source comprising a laser and a non-linear optical component having a spectral broadening effect on light from the laser, so that the illumination source is configured to illuminate the at least one wafer with a pulse of illumination of at least 1 ns, but no longer than 1 ps, in time and having a continuous spectral range of at least 20 nm; and
    c. a control system configured to adjust a spectrum of light illuminating the wafer in order to reduce the color variation in images of the wafer by controlling tuning means disposed in an optical path between the illumination source and the imager, the spectrum being adjusted to at least a first spectrum for inspection of the first region of the wafer and to a second spectrum for inspection of the second region of the wafer.

25. The method set forth in claim 19, further comprising: combining the illumination at each of the plurality of wavelength sub-bands into a single image after the blocking performed by each at least one filter mask.

26. The method as set forth in claim 19, wherein said step of illuminating a wafer with broadband illumination comprises illuminating a wafer with illumination having a continuous spectral range falling within a range from 180 nm to 450 nm.

27. The method as set forth in claim 19, wherein each of the plurality of wavelength sub-bands has a continuous spectral range of at least 50 nm.

* * * * *

UNITED STATES PATENT AND TRADEMARK OFFICE
CERTIFICATE OF CORRECTION

PATENT NO. : 7,659,973 B2  Page 1 of 1
APPLICATION NO. : 11/684191
DATED : February 9, 2010
INVENTOR(S) : Furman et al.

It is certified that error appears in the above-identified patent and that said Letters Patent is hereby corrected as shown below:

On page 23 of the patent in the Claims section:

Claim 1, column 19, line 24: replace "ps" with --µs--

Claim 13, column 20, line 32: replace "ps" with --µs--

On page 24 of the patent in the Claims section:

Claim 24, column 22, line 10: replace "ps" with --µs--

Signed and Sealed this

Twenty-ninth Day of June, 2010

David J. Kappos
*Director of the United States Patent and Trademark Office*